(12) United States Patent
Witte

(10) Patent No.: US 6,512,957 B1
(45) Date of Patent: Jan. 28, 2003

(54) CATHETER HAVING A GUIDE SLEEVE FOR DISPLACING A PRE-BENT GUIDEWIRE

(75) Inventor: Joachim Witte, Berlin (DE)

(73) Assignee: Biotronik Mess-und Therapiegeraete GmbH & Co. Ingenieurburo Berlin, Berlin (DE)

(*) Notice: Subject to any disclaimer, the term of this patent is extended or adjusted under 35 U.S.C. 154(b) by 0 days.

(21) Appl. No.: 09/603,089

(22) Filed: Jun. 26, 2000

(30) Foreign Application Priority Data

Jun. 25, 1999 (DE) .......................................... 199 30 266

(51) Int. Cl.[7] ................................................. A61N 1/05
(52) U.S. Cl. .............. 607/116; 604/164.13; 604/164.01; 600/585; 607/122
(58) Field of Search .................... 607/115–116, 119, 607/122–123, 126, 128; 600/372–375, 381, 585; 604/164.01, 164.09, 164.13, 264, 524–527; 606/108; 128/899

(56) References Cited

U.S. PATENT DOCUMENTS

| | | | |
|---|---|---|---|
| 4,103,690 A | | 8/1978 | Harris ........................ 128/418 |
| 5,376,109 A | | 12/1994 | Lindegren et al. .......... 607/122 |
| 5,381,790 A | | 1/1995 | Kanesaka .................... 128/642 |
| 5,387,233 A | * | 2/1995 | Alferness et al. ............ 607/122 |
| 5,423,884 A | | 6/1995 | Nyman et al. ............... 607/127 |
| 5,722,425 A | * | 3/1998 | Bostrom ..................... 600/585 |
| 5,752,915 A | * | 5/1998 | Neubauer et al. ........... 600/373 |
| 5,871,530 A | | 2/1999 | Williams et al. ............. 607/122 |
| 6,017,323 A | * | 1/2000 | Chee ........................... 604/249 |
| 6,192,280 B1 | * | 2/2001 | Sommer et al. ............. 607/122 |
| 6,210,408 B1 | * | 4/2001 | Chandrasekaran et al. .. 600/585 |

FOREIGN PATENT DOCUMENTS

| | | |
|---|---|---|
| DE | 31 00 545 | 7/1982 |
| DE | 31 50 052 | 7/1983 |
| DE | 35 07 119 | 8/1986 |
| DE | 91 03 081 | 7/1991 |
| DE | 38 89 635 | 9/1994 |
| DE | 43 33 090 | 3/1995 |
| EP | 0 468 645 | 1/1992 |
| EP | 0 667 126 | 8/1995 |
| EP | 0 773 037 | 5/1997 |
| EP | 0 778 043 | 6/1997 |
| WO | WO 98/02201 | 1/1998 |
| WO | WO 98/32375 | 7/1998 |
| WO | WO 99/06102 | 2/1999 |
| WO | WO 99/55412 | 11/1999 |

* cited by examiner

*Primary Examiner*—Kennedy Schaetzle
*Assistant Examiner*—Kristen Droesch
(74) *Attorney, Agent, or Firm*—Venable; Robert Kinberg; Catherine M. Voorhees

(57) ABSTRACT

A catheter for the introduction into blood vessels having a lumen and guide means arranged therein wherein the guide means include a pre-bent wire (26) displaceable in the longitudinal direction of the catheter (10) and the catheter (10) has at its distal end an exit lock means (38) such that the pre-bent wire (26) can issue from the catheter (10) through the exit lock means (38) at the distal end.

14 Claims, 5 Drawing Sheets

CATHETER HAVING A GUIDE SLEEVE FOR DISPLACING A PRE-BENT GUIDEWIRE

The invention concerns a catheter for the introduction into blood vessels having a lumen and guide means arranged therein.

BACKGROUND OF THE INVENTION

In this description the term catheter is also used for example to denote an electrode together with electrode line for cardiac pacemakers or defibrillators. A large number of various catheters of the kind set forth in the opening part of this specification are known, which are equipped with various guide means in order to direct a catheter through blood vessels to a desired location. Such catheters or electrodes are known for example from EP 0 667 126, U.S. Pat. Nos. 5,423,884, 5,367,109 or DE 35 107 119.

It has been found that known catheters, in particular known cardiac pacemaker electrodes, are scarcely suitable for being introduced for example into the coronary sinus of a heart. There is however the wish to be able also to introduce in particular a cardiac pacemaker electrode into the coronary sinus or blood vessels which involve similar difficulties of access.

SUMMARY OF THE INVENTION

Therefore the object of the present invention is to provide a catheter which is suitable for introduction into the coronary sinus or other blood vessels which involve difficult access, in particular a cardiac pacemaker electrode line.

In accordance with the invention, that object is achieved with a catheter of the kind set forth in the opening part of this specification, in which the guide means include a pre-bent wire displaceable in the longitudinal direction of the catheter and in which the catheter has at its distal end an exit lock means such that the prebent wire can issue from the catheter through the exit lock means at the distal end.

The invention is based on the notion of using the pre-bent wire as a probe which can be advanced beyond the tip of the catheter and which, by virtue of the prebent configuration of the wire, faces in a direction which differs from the straight-ahead direction of the catheter. It is possible In that way with the pre-bent wire, to advance into a branch of the blood vessels and to follow with the catheter which is then guided by the pre-bent wire. In this case, the pre-bent wire can be retracted into the catheter again to the same degree as the catheter is advanced so that the tip of the pre-bent wire does not need to execute any relative movement with respect to the blood vessel when the catheter follows along. An exit lock means at the tip of the catheter makes it possible to push out the pre-bent wire without any amount of body fluid worth mentioning penetrating into the catheter.

The pre-bent wire is preferably a spring steel wire. It is pre-bent in a helical or spiral configuration at least in the region of its distal end. That manner of pre-bending the wire makes it possible to afford various orientations for the wire, depending on how far the wire is advanced beyond the tip of the catheter. Spring steel wire is suitable for the reason that spring steel can be pre-bent and then the spring action of the spring steel can be straightened out again under the influence of suitable return forces, in which case when those return forces are released, the spring steel wire resumes its pre-bent shape.

Preferably the guide means include for the pre-bent wire a guide sleeve or casing which is of such a configuration that it holds the pre-bent wire within the catheter in a straight prestressed condition. The guide sleeve, for example a tube portion, into which the pre-bent wire is inserted, in this case exerts the return forces required for straightening the spring steel wire. When the spring steel wire is advanced out of the tube portion, those return forces which are exerted on the spring steel wire by the tube portion no longer act so that the spring steel wire curves in a configuration corresponding to its pre-bent shape as soon as it issues from the guide sleeve.

In this case, the pre-bent wire is preferably adapted to be rotatable relative to the rest of the catheter about its longitudinal axis and is connected to actuating means arranged at the proximal end of the catheter, for rotation of the pre-bent wire. If the pre-bent wire is pre-bent for example in a spiral configuration, it is possible by way of the actuating means to determine the radial direction in which the pre-bent wire is oriented upon being advanced beyond the tip of the catheter.

Preferably the catheter has a bar which is of a tubular configuration and which serves as a guide sleeve or casing, having an internal passage in which the pre-bent wire is guided. In that way the bar holds the guide wire oriented in the longitudinal direction of the catheter. The bar is preferably also arranged longitudinally slidably in the catheter and/or rotatably about its longitudinal axis and is connected to actuating means for producing the longitudinal sliding movement and/or the rotary movement of the bar. The pre-bent wire which is guided in the bar can also be rotated in the same way with the actuating means for rotating the bar so that the orientation of the pre-bent wire can be determined by way of the rotary movement of the bar. If the bar is for example in the form of a stylet for screwing in a screw-in tip for an electrode line, the bar and the pre-bent wire can also be adapted to be rotatable independently of each other.

Preferably the exit lock means includes a diaphragm or membrane which is to be pierced by the pre-bent wire. In that way the tip of the catheter can remain completely closed by the diaphragm until the pre-bent wire pierces the diaphragm and issues from the tip of the cathode at the front thereof. If the diaphragm comprises elastic material, for example silicone, it closes again when the pre-bent wire is retracted into the catheter again.

On its side towards the interior of the catheter the exit lock means preferably has an entrance opening for the pre-bent wire, which opening is of a funnel-shaped configuration. That makes it easier to introduce the tip of the pre-bent wire into the exit lock means.

The exit lock means preferably also has an exit opening in the outside of the catheter, which is in the center of a rounded catheter tip at the distal end of the catheter. Due to the central arrangement of the exit opening on the tip of the catheter, the orientation of the catheter itself, upon extension of the pre-bent wire, is irrelevant, the catheter behaves in the same manner in any rotational angular position. The rounded tip of the catheter contributes to the catheter being able to easily follow the pre-bent wire when following same, even in lateral blood vessels which involve a difficult access.

The pre-bent wire is preferably coated with gold so that it can be located for example by an X-ray device so that the pre-bent wire can be specifically controlled upon insertion of the catheter.

The catheter is preferably in the form of a cardiac pacemaker or defibrillator electrode.

BRIEF DESCRIPTION OF THE DRAWINGS

The invention will now be described by means of embodiments with reference to the accompanying drawings in which.

DETAILED DESCRIPTION OF THE INVENTION

Figure 1:
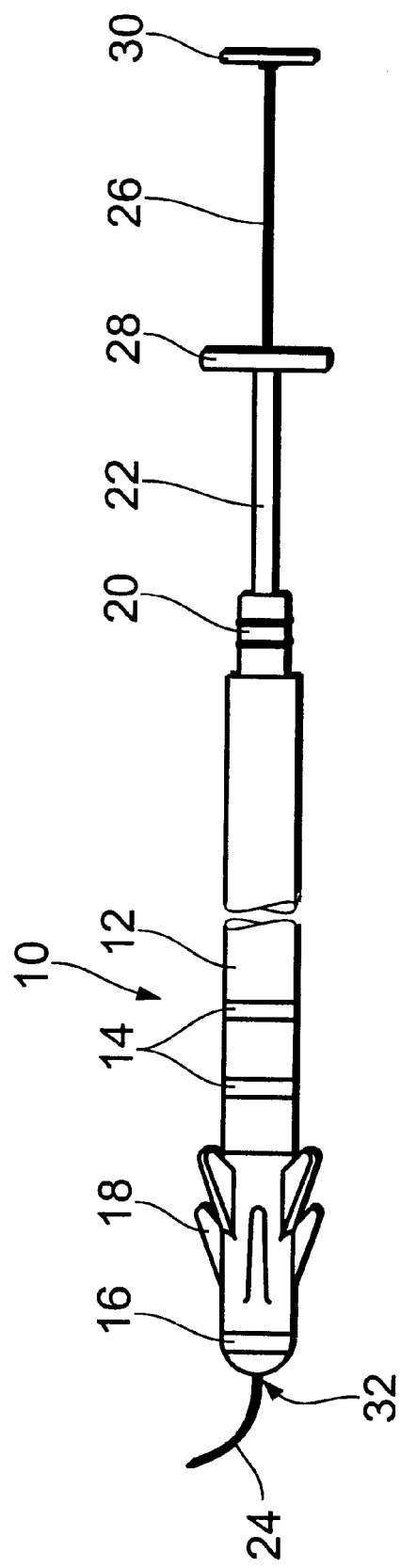
FIG. 1 is a diagrammatic outside view of a catheter with pre-bent guide wire.
Figure 1A:
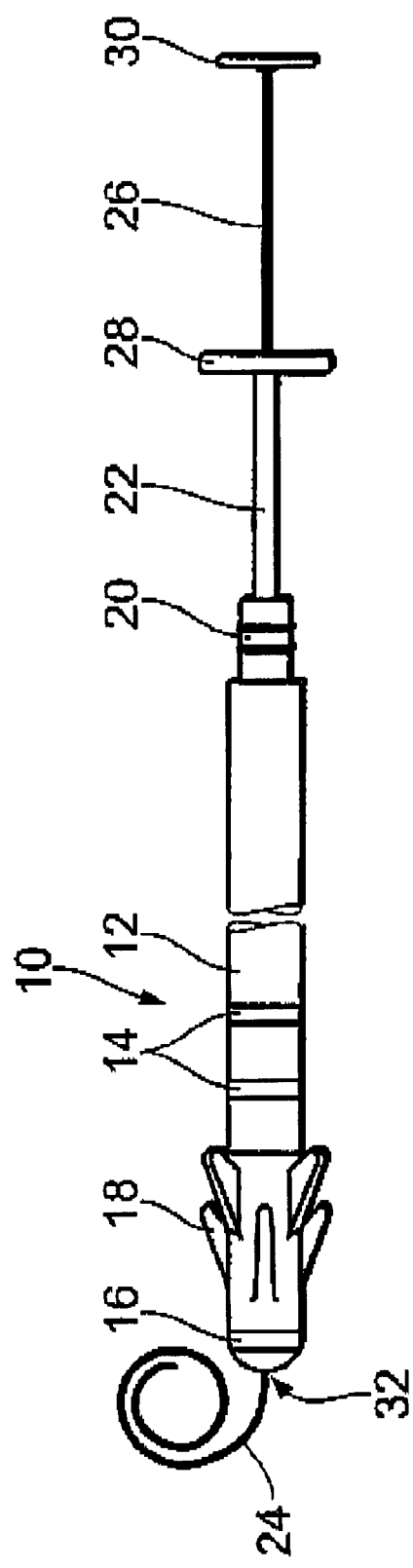
FIGS. 1a and 1b illustrate the spirally pre-bent and helically pre-bent embodiments of the invention, respectively.
Figure 1B:
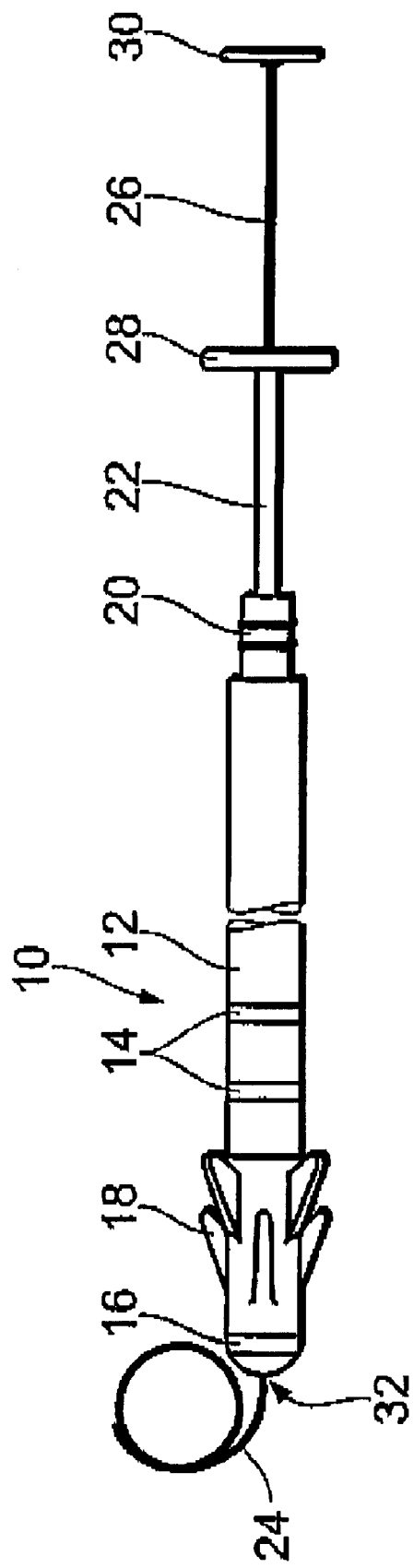

The catheter 10 which is illustrated in FIG. 1 is in the form of a cardiac pacemaker electrode with an electrode line 12, at the distal end of which are arranged ring electrodes 14 and a tip electrode 16. Also provided at the distal end of the electrode line 12 are tines 18 which can serve as spacer portions or anchoring means for the head of the electrode in the myocardium of a heart. The electrodes 14 and 16 are connected by way of a coiled electrical conductor arranged in the electrode line 12, to a plug connection 20 which serves for electrically connecting the catheter 10 to a stimulation device such as a cardiac pacemaker or a defibrillator.

Also extending in the electrode line 12 is a bar 22 which is of a tubular configuration with a passage extending in the interior of the bar 22. Extending in the passage is a wire 26 which is pre-bent at its distal end 24. Both the bar 22 and also the pre-bent wire 26 are respectively connected at their proximal ends to actuating means 28 and 30 which are diagrammatically illustrated in FIG. 1 and with which both the bar 22 and also the pre-bent wire 26 can be displaced relative to each other and relative to the electrode line 12 in the longitudinal direction thereof and rotated about the longitudinal axis thereof.

It can already be seen from FIG. 1 that the pre-bent wire 26 can be advanced with its distal end 24 beyond the tip 32 of the catheter 10. As the pre-bent wire 26 is pre-bent at its distal end 24, when it issues from the catheter tip 32 it curves into the pre-bend direction. This is a different direction from the extended longitudinal axis of the catheter 10, in the region of its distal end.

Upon insertion of the catheter 10 it can be advanced into the proximity for example of a blood vessel branching. Until then, the pre-bent wire 26 can remain completely retraced into the catheter 10 so that the catheter 10 terminates at its tip 32. In the proximity of the blood vessel branching the pre-bent wire can then be advanced beyond the tip 32 of the catheter and in so doing is laterally curved in the manner illustrated. By rotation of the pre-bent wire 26 alone or jointly with the bar 22, it is possible to select the ideal direction in which the pre-bent wire 26 departs from the notional extension of the distal end of the catheter 10 so that the distal end 24 of the pre-bent wire 26 can be introduced exactly into a branching blood vessel. In order to be able to optically follow that procedure outside a body which is to be treated, the pre-bent wire is coated with gold in the region of its distal end. That coating is compatible with the body and makes the pre-bent wire 26 visible by means of an X-ray apparatus. After the pre-bent wire 26 has been sufficiently far advanced with its distal end 24 into a branching blood vessel such as for example the coronary sinus of a heart, the catheter 10 can be followed on, with the pre-bent wire 26 being withdrawn into the catheter 10 at the same time. In that way it is possible for the pre-bent wire 26 not to involve any relative movement which could result in injuries, when the catheter 10 is being further inserted into the blood vessel.

The longitudinal section shown in the Figure through the distal end of the catheter 10 shows that distal end before the pre-bent wire 26 is pushed beyond the tip of the catheter 32. It is possible to see therein ring electrodes 14 and a coiled electric line 34 which serves for the transmission of electrical signals from and to the electrodes 14. Extending within the coiled electrode line 34 is the bar 22 which is of a tubular configuration and in whose internal passage 36 is guided the pre-bent wire 26. The pre-bent wire 26 is straightened by the bar 36 so that the pre-bent wire 26 extends substantially straight in the interior of the catheter 10.

Figure 2:
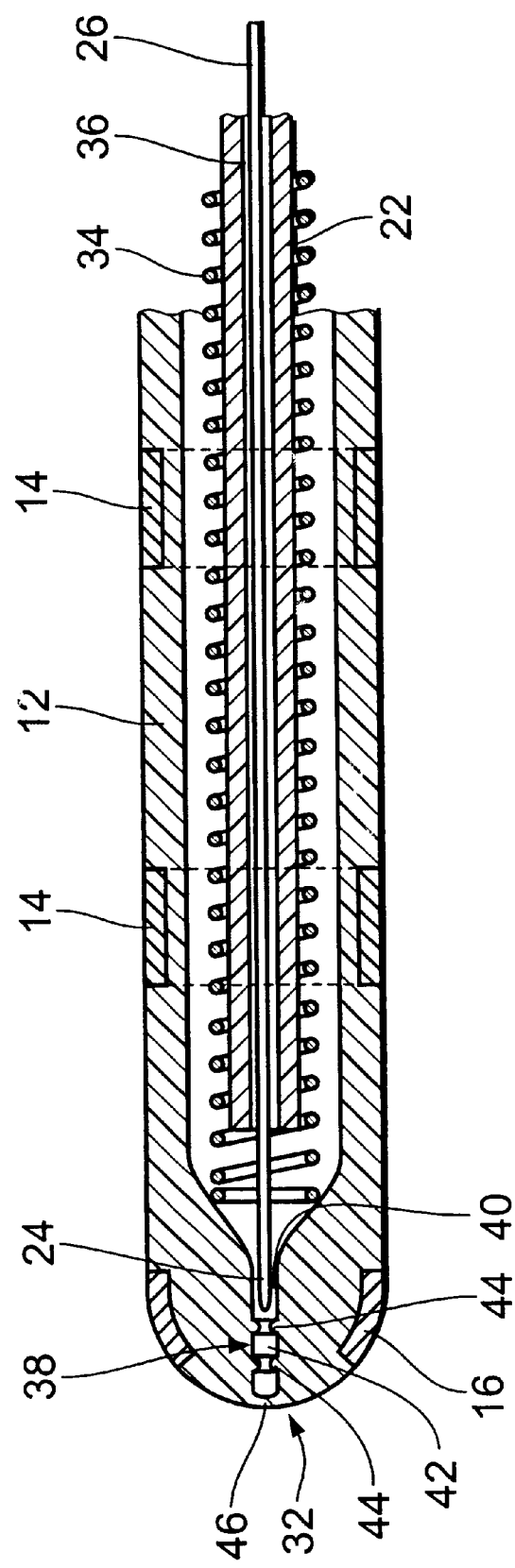
FIG. 2 is a view in section through the distal end of a catheter like that of FIG. 1.

As can be seen from FIG. 2, at its distal end the catheter 10 has an exit lock means 38 through which the pre-bent wire 26 can be pushed. At its side towards the interior of the catheter, the exit lock means 38 has an entrance opening 40 of a funnel-like configuration in order to guide the front end of the pre-bent wire 26 into an exit lock passage 42 which adjoins the entrance opening 40. Provided in the exit lock passage are sealing lips 44 which bear against the peripheral surface of the pre-bent wire 26 when the pre-bent wire 26 is introduced into the exit lock passage 42. When the pre-bent wire 26 is inserted into the exit lock passage 42, a condition of sealing integrity is afforded by means of the sealing lips 44.

It can further be seen from FIG. 2 that the exit lock passage 42 is closed in the region of the tip 32 of the catheter by a diaphragm 46 which is pierced when the pre-bent wire 26 is first advanced beyond the tip 32 of the catheter 10.

Figure 3:
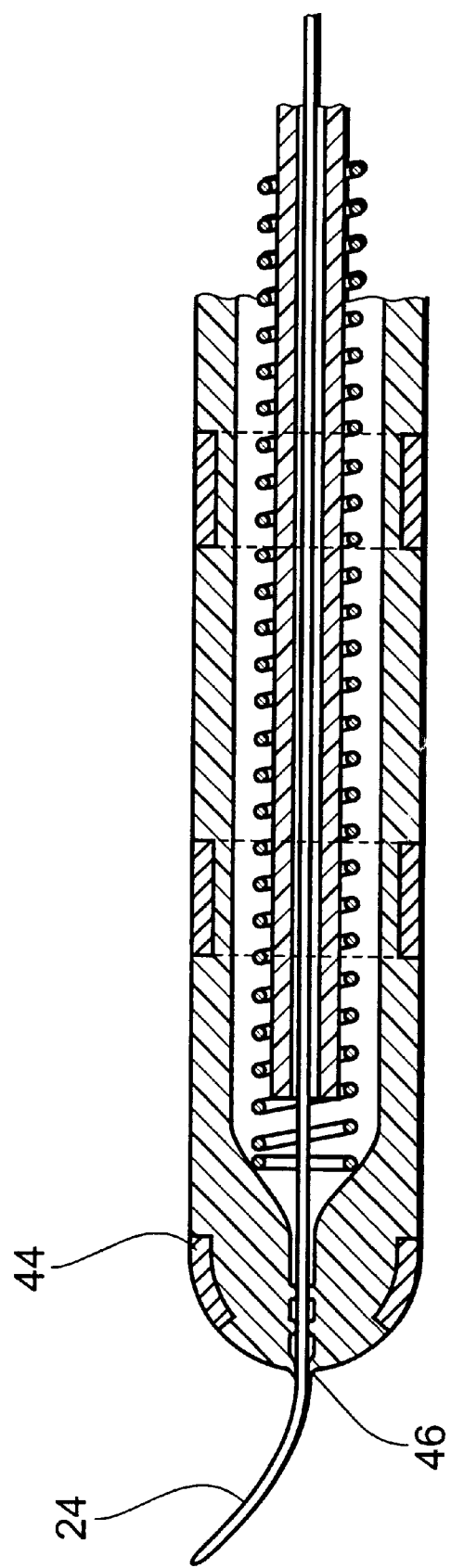
FIG. 3 shows the section of FIG. 2 with the pre-bent wire advanced.

That condition is shown in FIG. 3. As soon as the pre-bent wire 26 issues with its distal end 24 from the catheter 10, it is no longer subjected to forces which straighten it against its pre-stressing, so that the pre-bent wire curves freely in a configuration corresponding to its pre-bend shape. The pierced diaphragm 46 also represents a further sealing lip which, together with the sealing lips 44, provide for sealing integrity in respect of the interior of the catheter in relation to the exterior thereof.

What is claimed is:

1. A catheter for the introduction of an electrode line into blood vessels comprising:
    a catheter lumen having a distal end;
    guide means for guiding the catheter into the blood vessels, the guide means being disposed in the catheter lumen and including a pre-bent guide wire displaceable in the longitudinal direction of the catheter lumen, said pre-bent wire being straightened when inside the catheter lumen and resuming its pre-bent shape when outside the catheter lumen; and
    exit lock means for closing the distal end of the catheter lumen where the straightened pre-bent guide wire passes through the closed end of the catheter lumen and curves in a configuration corresponding to its pre-bent shape in order to advance into a branch of blood vessels.

2. A catheter as set forth in claim 1, wherein the pre-bent wire is a spring steel wire.

3. A catheter as set forth in claim 1 or claim 2, wherein the pre-bent wire has a distal end and is pre-bent helically at least in the region of its distal end.

4. A catheter as set forth in claim 1 or claim 2, wherein the pre-bent wire has a distal end and is pre-bent spirally at least in the region of its distal end.

5. A catheter as set forth in claim 1, wherein the guide means includes a guide sleeve for the pre-bent wire, said guide sleeve holding the pre-bent wire in a straight pre-stressed state within the catheter lumen.

6. A catheter as set forth in claim 5, wherein the guide means includes a bar which is of a tubular configuration and which serves as the guide sleeve and which has an internal passage in which the pre-bent wire is guided.

7. A catheter as set forth in claim 6, further comprising actuating means for longitudinally sliding movement and/or rotary movement of the bar wherein the bar is longitudinally slidable in the catheter and/or rotatable about its longitudinal axis and is connected to the actuating means for longitudinal sliding movement and/or rotary movement of the bar.

8. A catheter as set forth in claim 1, further comprising actuating means for rotating the pre-bent wire wherein the pre-bent wire is adapted to be rotatable relative to the rest of the catheter about its longitudinal axis and is connected to the actuating means arranged at a proximal end of the catheter.

9. A catheter as set forth in claim 1, wherein the exit lock means includes a diaphragm which is to be pierced by the pre-bent wire.

10. A catheter as set forth in claim 1, wherein on its side towards the interior of the catheter the exit lock means has an entrance opening for the pre-bent wire, the opening being of a funnel-shaped configuration.

11. A catheter as set forth in claim 1, wherein the catheter lumen has a rounded catheter tip and the exit lock means has an exit opening in the outside of the catheter lumen, which is in the center of the rounded catheter tip at the distal end of the catheter lumen.

12. A catheter as set forth in claim 1, wherein the catheter is in the form of a cardiac pacemaker electrode line or defibrillator electrode line.

13. A catheter as set forth in claim 1, wherein the pre-bent wire includes gold.

14. A catheter as set forth in claim 13, wherein the catheter lumen has a catheter tip at its distal end and at least a front end surface of the pre-bent wire is formed by gold which can be advanced beyond the catheter tip.

* * * * *